United States Patent
Pan et al.

(10) Patent No.: US 10,017,824 B2
(45) Date of Patent: Jul. 10, 2018

(54) METHOD FOR DETERMINING NUCLEIC ACID COMPOSITION OF NUCLEIC ACID MIXTURE

(71) Applicant: BGI GENOMICS CO., LIMITED, Shenzhen, Guangdong (CN)

(72) Inventors: Xiaoyu Pan, Shenzhen (CN); Jing Guo, Shenzhen (CN); Hui Jiang, Shenzhen (CN); Fang Chen, Shenzhen (CN); Shengpei Chen, Shenzhen (CN); Shida Zhu, Shenzhen (CN); Fan Fan, Shenzhen (CN); Jialou Zhu, Shenzhen (CN)

(73) Assignee: BGI GENOMICS CO., LIMITED, Shenzhen, Guangdong (CN)

( * ) Notice: Subject to any disclaimer, the term of this patent is extended or adjusted under 35 U.S.C. 154(b) by 12 days.

(21) Appl. No.: 14/908,695

(22) PCT Filed: Jul. 30, 2013

(86) PCT No.: PCT/CN2013/080419
§ 371 (c)(1),
(2) Date: Jan. 29, 2016

(87) PCT Pub. No.: WO2015/013885
PCT Pub. Date: Feb. 5, 2015

(65) Prior Publication Data
US 2016/0160288 A1 Jun. 9, 2016

(51) Int. Cl.
*C12Q 1/6853* (2018.01)
*C12Q 1/6881* (2018.01)
(Continued)

(52) U.S. Cl.
CPC ......... *C12Q 1/6886* (2013.01); *C12Q 1/6827* (2013.01); *C12Q 1/6851* (2013.01);
(Continued)

(58) Field of Classification Search
None
See application file for complete search history.

(56) References Cited

U.S. PATENT DOCUMENTS

2005/0239101 A1* 10/2005 Sukumar ............... C12Q 1/686
                                                               435/6.12
2009/0220980 A1*  9/2009 Hoon ................... C12Q 1/6886
                                                               435/6.12

FOREIGN PATENT DOCUMENTS

CN    102311953 A    1/2012
WO    03062441 A1    7/2003

OTHER PUBLICATIONS

Swift-Scanlan et al. BioTechniques. 2006. 40:210-219.*
(Continued)

*Primary Examiner* — Joseph G. Dauner
(74) *Attorney, Agent, or Firm* — Panitch Schwarze Belisario & Nadel LLP (57) ABSTRACT

The present invention provides a method for determining the nucleic acid composition in a total nucleic acid mixture comprising a first nucleic acid and a second nucleic acid. The method comprises: 1) treating the total nucleic acid mixture with a bisulfate, to convert the non-methylated cytosine in the total nucleic acid mixture into uracil, and obtain a converted total nucleic acid mixture; 2) subjecting the converted total nucleic acid mixture to multiplexed fluorescent quantitative PCR using a first set of amplification primers and a second set of amplification primers; and 3) based on the ratio R of the methylated amplification product to the non-methylated amplification product of the predetermined nucleic acid fragment, a methylation proportion $M_1$ of the predetermined nucleic acid fragment in the first nucleic acid, and a methylation proportion $M_2$ of the pre-
(Continued)

determined nucleic acid fragment in the second nucleic acid, determining the nucleic acid composition in the total nucleic acid mixture.

17 Claims, 1 Drawing Sheet

(51) Int. Cl.
    *C12Q 1/6886*     (2018.01)
    *C12Q 1/6827*     (2018.01)
    *C12Q 1/6876*     (2018.01)
    *C12Q 1/6851*     (2018.01)

(52) U.S. Cl.
    CPC ......... *C12Q 1/6876* (2013.01); *C12Q 1/6881* (2013.01); *C12Q 2600/154* (2013.01); *C12Q 2600/158* (2013.01); *C12Q 2600/16* (2013.01)

(56) References Cited

OTHER PUBLICATIONS

Park et al. Int. J. Cancer. 2008. 122:2498-2502.*
Zhang et al. J Huazhong Univ Sci Technol. 2011. 31(5):687-692.*
Ragione et al. Journal of Molecular Diagnostics. 2010. 12(6):797-807.*
Fackler et al. Cancer Research. 2004. 64(13):4442-4452.*
Endoh et al. Int. J. Cancer. 2003. 106:45-51.*
Wong et al. International Journal of Oncology. 2006. 28:767-773.*
Int'l Search Report and Written Opinion dated May 20, 2014 in Int'l Application No. PCT/CN2013/080419.

* cited by examiner

METHOD FOR DETERMINING NUCLEIC ACID COMPOSITION OF NUCLEIC ACID MIXTURE

CROSS-REFERENCE TO RELATED APPLICATION

This application is a Section 371 of International Application No. PCT/CN2013/080419, filed Jul. 30, 2013, which was published in the Chinese language on Feb. 5, 2015, under International Publication No. WO 2015/013885 A1, and the disclosure of which is incorporated herein by reference.

REFERENCE TO SEQUENCE LISTING SUBMITTED ELECTRONICALLY

This application contains a sequence listing, which is submitted electronically via EFS-Web as an ASCII formatted sequence listing with a file name "Sequence_Listing.TXT", creation date of Jan. 26, 2016, and having a size of 5.1 kilobytes. The sequence listing submitted via EFS-Web is part of the specification and is herein incorporated by reference in entirety.

BACKGROUND

Technical Field

The present invention relates to the field of biological technology, particularly to a method for determining nucleic acid composition in a nucleic acid mixture, and more specifically to a method for determining the content of a first nucleic acid in a total nucleic acid mixture comprising the first nucleic acid and a second nucleic acid.

Related Art

Prenatal diagnosis is one of the most efficient ways to reduce congenital anomalies by diagnosing congenital defects or genetic diseases in a fetus before birth using various detection tools, for example, imaging, biochemical, cytogenetic, and molecular biological technologies.

Since 1997, research has shown that cell-free fetal DNA is present in the peripheral blood of a pregnant woman, and this finding generates a new opportunity for noninvasive fetal screening.

In the existing method for detecting fetal chromosomal aneuploidy by sequence analysis of the maternal plasma, the total free DNA in the maternal plasma is generally sequenced, without making a discrimination between the fetal and maternal DNA, and whether the fetus has chromosomal aneuploidy is determined using a significance test. The method has certain advantages in noninvasive screening of trisomies. However, when the fetal DNA concentration is low, a false negative result may potentially be obtained due to a low significance of the chromosomal abnormality.

Therefore, there is a need for an improved method for quantifying the fetal DNA in the maternal plasma.

DNA methylation refers to a chemical modification process in which in the presence of a DNA methyl transferase, a methyl group is added to the C-5 carbon of cytosine, to produce methylcytosine. Such a DNA methylation modification may be individual-, tissue- or cell-specific, such that the DNA from different sources (for example, fetal versus maternal DNA, or tumor versus normal DNA) can be discriminated based on the methylation of a particular gene, allowing the DNA from a source to be quantified.

For detection of cancers at an early stage, the methylation of a particular gene is closely linked to the occurrence and development of cancers, and thus can be used as a potential marker in early diagnosis. For example, colorectal cancer, also referred to as large intestine cancer, involves the proliferation of tumors in the large intestine, the rectum and the appendix. In the western world, it is the third most prevalent cancer, and the second leading cancer-causing death. Generally, it is thought that many large intestine cancers originate from the adenomatous polyp of the large intestine. These mushroom-like tumors are generally benign, but some of them develop into cancers after a period of time. Colon cancer may be effectively treated at an early stage by surgical operation before metastasis, to prolong survival time. Therefore, the detection of colorectal cancer at an early stage is a key factor determining whether a successful and absolute cure can be achieved. A highly specific and sensitive marker is crucial for the diagnosis of colorectal cancers. For example, qualitative and quantitative detection of abnormally high DNA methylation in serum and excrements is a new, highly promising, and non-invasive method for screening for colorectal cancer.

SUMMARY

The present invention aims to solve at least one of the technical problems above to some extent or to provide at least a useful commercial option. For this purpose, an objective of the present invention is to provide a method for effectively determining nucleic acid composition in a nucleic acid mixture comprising nucleic acids from a variety of sources.

The present invention provides a method for determining nucleic acid composition in a total nucleic acid mixture comprising a first nucleic acid and a second nucleic acid, in which the first nucleic acid and the second nucleic acid are derived from different sources, including, but not limited to, different individuals, different tissues, and different cells. According to an embodiment of the present invention, the method comprises: 1) treating the total nucleic acid mixture with a bisulfite to convert the non-methylated cytosine in the total nucleic acid mixture into uracil, and to obtain a converted total nucleic acid mixture; 2) subjecting the converted total nucleic acid mixture to multiplexed fluorescent quantitative PCR using a first set of amplification primers and a second set of amplification primers to capture and amplify a predetermined nucleic acid fragment, and to obtain a ratio R of a methylated amplification product to a non-methylated amplification product of the predetermined nucleic acid fragment, in which the first nucleic acid and the second nucleic acid both contain the predetermined nucleic acid fragment, and the predetermined nucleic acid fragment in the first nucleic acid differs from the predetermined nucleic acid fragment in the second nucleic acid in terms of the methylation level; the first set of amplification primers specifically recognize the converted predetermined nucleic acid fragment, and the second set of amplification primers specifically recognize the unconverted predetermined nucleic acid fragment; and a methylation proportion $M_1$ of the predetermined nucleic acid fragment in the first nucleic acid and a methylation proportion $M_2$ of the predetermined nucleic acid fragment in the second nucleic acid are predetermined; and 3) determining the nucleic acid composition in the total nucleic acid mixture based on the ratio R of the methylated amplification product to the non-methylated amplification product of the predetermined nucleic acid fragment, the methylation proportion $M_1$ of the predetermined nucleic acid fragment in the first nucleic acid, and the methylation proportion $M_2$ of the predetermined nucleic acid fragment in the second nucleic acid.

According to an embodiment of the present invention, the treatment of DNA with a bisulfite allows the non-methylated cytosine to be converted into uracil by deamination, while the cytosine protected with a methyl group remains unchanged, such that a methylated cytosine site can be discriminated from a non-methylated cytosine site. Further, after PCR, the original methylated cytosine remains unchanged, and the uracil obtained after treatment with a bisulfite is completely converted into thymine. Therefore, a methylated fragment or a non-methylated fragment in the DNA obtained after treatment with a bisulfite can be specifically amplified by designing a methylation specific or non-methylation specific PCR primer. The number of methylated fragments and non-methylated fragments correlates with the composition ratio of nucleic acid molecules from different sources, allowing the composition of nucleic acid molecules from different sources, for example, the content of a first nucleic acid or a second nucleic acid, in the nucleic acid mixture to be effectively determined using the method according to the present invention.

According to an embodiment of the present invention, the method can further have the following additional technical features.

In an embodiment according to the present invention, the first nucleic acid is a fetal DNA, and the second nucleic acid is a maternal DNA. Optionally, the total nucleic acid mixture is from maternal plasma DNA. Accordingly, the fetal DNA concentration in the mixture of maternal and fetal DNA can be effectively determined. In some other embodiments of the present invention, the first nucleic acid is a cancer cell DNA, and the second nucleic acid is a non-cancer cell DNA. Optionally, the total nucleic acid mixture is present in a tissue, plasma, or fecal DNA sample from a tumor patient. Therefore, the methylation level in cancer tissues of tumor patients can be analyzed.

In an embodiment according to the present invention, the contents of the first nucleic acid in the total nucleic acid mixture is determined in Step 3) according to the formula $\varepsilon=(M_2+RM_2-R/[R(M_2-M_1)-(M_1-M_2)]$ to thereby effectively determine the composition and content of nucleic acid molecules in the total nucleic acid mixture.

In an embodiment according to the present invention, $M_1$ is at least 10×, preferably at least 50×, more preferably at least 90×, and most preferably at least 100× the value of $M_2$ to thereby further improve the efficiency with which the composition and content of the nucleic acid molecules are determined.

In an embodiment according to the present invention, the contents of the first nucleic acid in the total nucleic acid mixture is determined in Step 3) according to the formula $\varepsilon=R/[M_1R+M_1]$ to thereby further simplify the method for determining the composition and content of nucleic acid molecules in the total nucleic acid mixture, and further improve the efficiency with which the composition and content of the nucleic acid molecules in the total nucleic acid mixture are determined.

In an embodiment according to the present invention, the predetermined nucleic acid fragment includes one or more nucleic acid fragments located on different chromosomes.

In an embodiment according to the present invention, the predetermined nucleic acid fragment includes one or more nucleic acid fragments located on different genes. In an embodiment according to the present invention, the predetermined nucleic acid fragment can be selected from at least a portion of a gene of RASSF1A, SERPINB5, C21orf63, OLIG2, CBR1, SIM2, DSCAM, TRPM2, C21orf29, COL18A1, AIRE, ERG, CD48, FAIM3, ARHGAP25, BMP3, VIM, NDRG4, TFPI2, SFRP2, SEPT9, or SELPLG. Therefore, the method can be effectively used in prenatal and tumor screening. According to an embodiment of the present invention, for various genes, the predetermined nucleic acid fragment includes at least one selected from the nucleic acid sequences shown below:

| Gene | Nucleic acid sequence |
| --- | --- |
| RASSF1A | chr3: 50378097-50378226 |
| AIRE | chr21: 45703903-45704111 |
| SIM2 | chr21: 38078780-38079213 |
| ERG | chr21: 39878777-39879107 |
| CD48 | chr1: 160681560-160681732 |
| FAIM3 | chr1: 207096473-207096654 |
| ARHGAP25 | chr2: 69001823-69002052 |
| SELPLG | chr12: 109028663-109028901 |
| BMP3 | chr4: 81951942-81952808 |
| VIM | chr10: 17270431-17272617 |
| NDRG4 | chr16: 58497034-58498595 |
| TFPI2 | chr7: 93519367-93520184 |
| SFRP2 | chr4: 154709513-154710827 |
| SEPT9 | chr17: 75368689-75370506 |

Accordingly, the fetal DNA concentration in a mixture of maternal and fetal DNA, or the concentration of the cancer cell DNA in a mixture of cancer cell and non-cancer cell DNA derived from a tumor tissue of a tumor patient can be effectively determined. In an embodiment according to the present invention, for a RASSF1A gene, the first set of amplification primers include nucleic acid molecules as shown in SEQ ID NOs: 7 and 8. Accordingly, the fetal DNA concentration in a mixture of maternal and fetal DNA, or the concentration of the cancer cell DNA in a mixture of cancer cell and non-cancer cell DNA derived from a tumor tissue can be effectively determined.

In an embodiment according to the present invention, for a RASSF1A gene, the second set of amplification primers include nucleic acid molecules as shown in SEQ ID NOs: 4 and 5. Accordingly, the fetal DNA concentration in a mixture of maternal and fetal DNA, or the concentration of the cancer cell DNA in a mixture of cancer cell and non-cancer cell DNA derived from a tumor tissue can be effectively determined.

In an embodiment according to the present invention, a methylation specific probe and a non-methylation specific probe are further used in the multiplexed fluorescent quantitative PCR to thereby further improve the efficiency of the fluorescent quantitative PCR.

In an embodiment according to the present invention, a methylation specific probe and a non-methylation specific probe each bear a marker selected from at least one of FAM, JOE, and TAMRA to thereby further improve the efficiency of the fluorescent quantitative PCR.

In an embodiment according to the present invention, a methylation specific probe has a sequence as shown in SEQ ID NO: 6, and a non-methylation specific probe has a sequence as shown in SEQ ID NO: 9 to thereby further improve the efficiency of the fluorescent quantitative PCR.

In an embodiment according to the present invention, a methylation specific probe is marked with FAM and TAMRA to thereby further improve the efficiency of the fluorescent quantitative PCR. In an embodiment according to the present invention, a non-methylation specific probe is marked with JOE and TAMRA to thereby further improve the efficiency of the fluorescent quantitative PCR.

Accordingly, a method according to the present invention has at least the following advantages:

1. The content of a specific DNA in a DNA specimen from a subject can be assayed by a method according to an embodiment of the present invention using methylation specific multiplexed quantitative PCR.

2. Methods according to embodiments of the present invention are rapid and convenient. A method according to an embodiment of the present invention includes only a few steps, practically merely including options of DNA extraction, bisulfite treatment and quantitative PCR (QPCR). The convenience of the method makes a method according to the embodiment of the present invention applicable to various types of clinical detection (for example, detection of the fetal DNA in maternal plasma, or the detection of DNA content in tumor cells in specimens from tumor patients). The quickness of the method allows a method according to the embodiment of the present invention to be potentially applicable to quality control analysis of various types of clinical detection (for example, non-invasive prenatal diagnosis).

3. A method according to an embodiment of the present invention has a high throughput. The present invention involves a method for quantification by (but not limited to) QPCR, which has the advantage of high throughput. For example, using Applied Biosystems® StepOne™ or StepOnePlus™ Real-Time PCR Systems, up to 96 samples can be analyzed in one QPCR procedure.

4. A method according to an embodiment of the present invention has extendibility. A method according to the present invention involves analyzing content of a specific DNA in a DNA specimen from a subject by methylation specific multiplexed QPCR. For example, when multiple methylation markers (on different chromosomes) are used in the present invention, the variation in copy number of a specific DNA (for example, T21) of some chromosomes in the DNA specimen of a subject can be detected while the content of a specific DNA in the DNA specimen from the subject is being analyzed. It should be noted that the term "methylation marker" as used herein refers to a nucleic acid fragment that significantly differs in methylation level in nucleic acids from different sources. At least a portion of the gene RASSF1A, SERPINB5, C21orf63, OLIG2, CBR1, SIM2, DSCAM, TRPM2, C21orf29, COL18A1, AIRE, ERG, CD48, FAIM3, ARHGAP25, BMP3, VIM, NDRG4, TFPI2, SFRP2, SEPT9 or SELPLG mentioned above, or nucleic acid fragments in the table below can be used as a "methylation marker".

| Gene | Nucleic acid sequence |
|---|---|
| RASSF1A | chr3: 50378097-50378226 |
| AIRE | chr21: 45703903-45704111 |
| SIM2 | chr21: 38078780-38079213 |
| ERG | chr21: 39878777-39879107 |
| CD48 | chr1: 160681560-160681732 |
| FAIM3 | chr1: 207096473-207096654 |
| ARHGAP25 | chr2: 69001823-69002052 |
| SELPLG | chr12: 109028663-109028901 |
| BMP3 | chr4: 81951942-81952808 |
| VIM | chr10: 17270431-17272617 |
| NDRG4 | chr16: 58497034-58498595 |
| TFPI2 | chr7: 93519367-93520184 |
| SFRP2 | chr4: 154709513-154710827 |
| SEPT9 | chr17: 75368689-75370506 |

Additional aspects and advantages of the present invention will be partly given in, and partly apparent from, the description below, or understood through the practice of the present invention.

BRIEF DESCRIPTION OF THE DRAWINGS

The above and/or other additional aspects and advantages of the present invention become apparent and comprehensible from the description of embodiments in connection with the accompanying drawings, in which.

DETAILED DESCRIPTION

Embodiments of the present invention will be exemplarily described in detail hereinafter with reference to accompanying drawings in which the same or like reference characters refer to the same or like elements or elements having the same or like functions throughout. The embodiments described below with reference to accompanying drawings are exemplary, and intended to explain, rather than limit the present invention.

The terms "first" and "second" are used herein for purposes of description, and are not intended to indicate or imply relative importance or implicitly point out the number of the indicated technical feature. Therefore, the features defined by "first", and "second" may explicitly or implicitly include one or more features. In the description of the present invention, "plural" means two or more, unless it is defined otherwise specifically.

Figure 1:
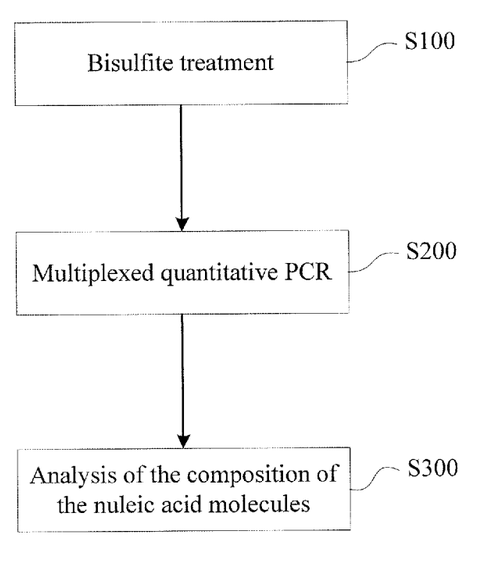
FIG. 1 is a schematic flow chart of a method for analyzing a total nucleic acid mixture according to an embodiment of the present invention.

Referring to FIG. 1, a method for analyzing a nucleic acid mixture according to the present invention is described in detail.

As shown in FIG. 1, the present invention provides a method for determining the nucleic acid composition in a total nucleic acid mixture. The total nucleic acid mixture comprises a first nucleic acid and a second nucleic acid. Specifically, the method comprises the following steps.

S100: Bisulfite Treatment

In this step, the total nucleic acid mixture is treated with a bisulfite to convert non-methylated cytosine in the total nucleic acid mixture into uracil, and to obtain a converted total nucleic acid mixture. During the step, the target region/fragment in the total nucleic acid mixture can be captured in advance if needed, and then treated with a bisulfite.

According to an embodiment of the present invention, the type of the total nucleic acid mixture that can be treated and analyzed by a method according to the present invention is not particularly limited, as long as the nucleic acid molecules from various sources contained in the total nucleic acid mixture have different methylation levels, and particularly different methylation levels exist for the same sequence. For example, according to an embodiment of the present invention, the total nucleic acid mixture can be a mixture of fetal and maternal DNA, or a mixture of cancer cell and non-cancer cell DNA. Thus, the total nucleic acid mixture can be a maternal plasma DNA, or a tissue, plasma or fecal DNA from a tumor patient. Specifically, in an embodiment according to the present invention, the first nucleic acid is a fetal DNA, and the second nucleic acid is a maternal DNA. Optionally, the total nucleic acid mixture is a maternal plasma DNA. Accordingly, the fetal DNA concentration in the mixture of maternal and fetal DNA can be effectively determined. In some other embodiments of the present invention, the first nucleic acid is a cancer cell DNA, and the second nucleic acid is a non-cancer cell DNA. The total nucleic acid mixture is a tissue, plasma, or fecal DNA from a tumor patient. Therefore, the methylation level in cancer tissues of tumor patients can be assayed.

According to an embodiment of the present invention, the method for extracting the DNA mixture from relevant biological samples is not particularly limited. For example, the DNA mixture can be extracted by a conventional DNA extraction method such as a salting-out method, column chromatography, a magnetic bead method, and an SDS method. Among the methods, the magnetic bead method is preferred. Briefly, the magnetic bead method comprises the following steps. Naked DNA molecules are obtained after the blood, tissues or cells are treated with proteinase K in a cell lysis buffer. The DNA molecules are subjected to reversible affinity adsorption using specific magnetic beads. The proteins, lipids, and other impurities are removed by washing with a detergent. The DNA molecules are then eluted from the magnetic beads using an eluant.

After the total nucleic acid mixture is obtained, the obtained mixture can be directly treated with a bisulfite, or the target region/fragment from the total nucleic acid mixture can be captured in advance if needed, and then treated with a bisulfite. According to an embodiment of the present invention, the treatment of DNA with a bisulfite allows non-methylated cytosines to be converted into uracils by deamination, while cytosines protected with a methyl group remain unchanged, such that a methylated cytosine site can be discriminated from a non-methylated cytosine site. Therefore, the subsequent analysis of a region comprising a methylated site or a non-methylated site can be effectively carried out. According to an embodiment of the present invention, the bisulfite treatment can be accomplished by any know methods, provided that the non-methylated cytosine can be converted into uracil by deamination, while the cytosine protected with a methyl group remains unchanged.

S200: Multiplexed Quantitative PCR

After the nucleic acid mixture is converted by treatment with a bisulfite, the relative proportions of the methylated fragment and the non-methylated fragment in the converted total nucleic acid mixture are analyzed by multiplexed PCR. Specifically, the converted total nucleic acid mixture is subjected to multiplexed fluorescent quantitative PCR using a first set of amplification primers and a second set of amplification primers, to determine a ratio R of a methylated amplification product and a non-methylated amplification product of the predetermined nucleic acid fragment.

The term "predetermined nucleic acid fragment" as used herein is a nucleic acid fragment that differs in methylation levels between a first nucleic acid and a second nucleic acid. According to an embodiment of the present invention, the first set of amplification primers specifically recognizes the converted predetermined nucleic acid fragment, and the second set of amplification primers specifically recognizes the unconverted predetermined nucleic acid fragment.

In an embodiment according to the present invention, the predetermined nucleic acid fragment includes one or more nucleic acid molecules located on different chromosomes.

In an embodiment according to the present invention, the predetermined nucleic acid fragment includes one or more nucleic acid fragments located on different genes. According to an embodiment of the present invention, the predetermined nucleic acid fragment can be selected from at least a portion of a gene of RASSF1A, SERPINB5, C21orf63, OLIG2, CBR1, SIM2, DSCAM, TRPM2, C21orf29, COL18A1, AIRE, ERG, CD48, FAIM3, ARHGAP25, BMP3, VIM, NDRG4, TFPI2, SFRP2, SEPT9, or SELPLG. Accordingly, the fetal DNA concentration in a mixture of maternal and fetal DNA, or the concentration of the cancer cell DNA in a mixture of cancer cell and non-cancer cell DNA derived from a tumor tissue can be effectively determined. According to an embodiment of the present invention, for various genes, the predetermined nucleic acid fragment includes at least one selected from the nucleic acid sequences shown below:

| Gene | Nucleic acid sequence |
|------|----------------------|
| RASSF1A | chr3: 50378097-50378226 |
| AIRE | chr21: 45703903-45704111 |
| SIM2 | chr21: 38078780-38079213 |
| ERG | chr21: 39878777-39879107 |
| CD48 | chr1: 160681560-160681732 |
| FAIM3 | chr1: 207096473-207096654 |
| ARHGAP25 | chr2: 69001823-69002052 |
| SELPLG | chr12: 109028663-109028901 |
| BMP3 | chr4: 81951942-81952808 |
| VIM | chr10: 17270431-17272617 |
| NDRG4 | chr16: 58497034-58498595 |
| TFPI2 | chr7: 93519367-93520184 |
| SFRP2 | chr4: 154709513-154710827 |
| SEPT9 | chr17: 75368689-75370506 |

It should be understood by those of skill in the art that the nucleic acid sequences in the table above are described by the positions of the sequences on each chromosome of the genome. For example, the nucleic acid sequence chr3: 50378097-50378226 of the RASSF1A gene refers to the nucleic acid sequence from positions 50378097 to 50378226 on chr3 of the human genome, that is, the nucleic acid sequence: accagctgccgtgtggggttgcacgcggtgccccgcgcgat-gcgcagegcgttggcacgctccagccgggtgeggccettccc agcgcgccca-gcgggtgccagctcccgcagctcaatgagctcaggct (SEQ ID NO: 1).

The term "multiplexed fluorescent quantitative PCR" as used herein can be referred to as methylation specific multiplexed QPCR, which is an experimental method by which a methylated and a non-methylated DNA fragment from a methylation marker can be amplified, and fluorescently quantified. During QPCR, the principle underlying the real-time fluorescent quantification is a probe method, in which the probe is an oligonucleotide probe that is tagged with a fluorescent reporter and a fluorescent quencher at the two ends, respectively. During PCR amplification, one specific fluorescent probe is added at the same time that a pair of primers is added. When the probe is intact, the florescent signal emitted from the reporter is absorbed by the quencher. During PCR amplification, the probe is enzymatically cleaved by the 5'-3' exonuclease activity of the Taq enzyme, such that the florescent reporter disassociates from the florescent quencher, whereby a florescence detection system can detect a fluorescent signal. During PCR amplification, a fluorescent molecule is formed for each DNA chain that is amplified, and thus the intensity of the fluorescent signal is proportional to the number of DNA molecules binding to the probe. As described above, in the multiplexed QPCR according to the present invention, the two sets of primers are designed such that the methylated and non-methylated DNA fragments in the methylation marker are both amplified, and the two kinds of DNA are quantified relatively using the methylation probe that specifically binds to the methylated fragment, and the non-methylation probe that specifically binds to the non-methylated fragment. Therefore, in an embodiment according to the present invention, a methylation specific probe and a non-methylation specific probe are further used in the multiplexed fluorescent quantitative PCR to thereby further improve the efficiency of the fluorescent quantitative PCR. In an embodiment according to the present invention, a methylation specific probe and a non-methylation specific probe each bear a marker selected from at least one of FAM, JOE, and TAMRA to thereby further improve the efficiency of the fluorescent quantitative PCR. In an embodiment according to the present invention, the methylation specific probe has a sequence as shown in SEQ ID NO: 6, and the non-methylation specific probe has a sequence as shown in SEQ ID NO: 9 to thereby further improve the efficiency of the fluorescent quantitative PCR. In an embodiment according to the present invention, the methylation specific probe is marked with FAM and TAMRA to thereby further improve the efficiency of the fluorescent quantitative PCR. In an embodiment according to the present invention, the non-methylation specific probe is marked with JOE and TAMRA to thereby further improve the efficiency of the fluorescent quantitative PCR.

In an embodiment according to the present invention, for the RASSF1A gene, the first set of amplification primers preferably includes nucleic acid molecules as shown in SEQ ID NOs: 7 and 8. For the RASSF1A gene, the second set of amplification primers preferably includes nucleic acid molecules as shown in SEQ ID NOs: 4 and 5. Accordingly, the fetal DNA concentration in the mixture of maternal and fetal DNA can be effectively determined.

The analysis of the relative contents of different fragments using multiplexed quantitative PCR can be carried out by any known methods. For example, the method and the relative standard curve method may be used. In the present invention, preferably $2^{-\Delta\Delta ct}$ method is preferably used to calculate the ratio of the methylated fragment to the non-methylated fragment, which is then calibrated by a standard curve.

According to an embodiment of the present invention, the preceding two steps can be conducted in parallel or in advance for particular nucleic acids, for example, the first nucleic acid and the second nucleic acid, to predetermine a methylation proportion $M_1$ of the predetermined nucleic acid fragment in the first nucleic acid, and a methylation proportion $M_2$ of the predetermined nucleic acid fragment in the second nucleic acid.

S300: Analysis of Composition of Nucleic Acid Molecules

The number of the methylated fragment and non-methylated fragment correlates with the composition ratio of nucleic acid molecules from different sources. After determining the methylation proportion $M_1$ of a predetermined nucleic acid fragment in the first nucleic acid and the methylation proportion $M_2$ of the predetermined nucleic acid fragment in the second nucleic acid, and determining the ratio R of the methylated amplification product to the non-methylated amplification product of the predetermined nucleic acid fragment by multiplexed fluorescent quantitative PCR, the composition of the nucleic acid molecules, for example, the content of the first nucleic acid or the second nucleic acid, can be effectively determined through data analysis.

According to an embodiment of the present invention, the content E of the first nucleic acid in the total nucleic acid mixture is determined in this step according to the formula $\varepsilon=(M_2+RM_2-R)/[R(M_2-M_1)-(M_1-M_2)]$ to thereby effectively determine the composition and content of nucleic acid molecules in the total nucleic acid mixture.

In an embodiment according to the present invention, a predetermined nucleic acid fragment that differs significantly in methylation level in the first nucleic acid and the second nucleic acid can be used. For example, $M_1$ is at least 10×, preferably at least 50×, more preferably at least 90×, and most preferably at least 100× the value of $M_2$ to thereby further improve the efficiency with which the composition and content of the nucleic acid molecules are determined since the value of $M_2$ is small and can be ignored without influencing the final result. Accordingly, in an embodiment according to the present invention, the content ε of the first nucleic acid in the total nucleic acid mixture can be determined according to the formula $\varepsilon=R/[M_1R+M_1]$ in this step to thereby further simplify the method for determining the composition and content of nucleic acid molecules in the total nucleic acid mixture, and further improve the efficiency with which the composition and content of the nucleic acid molecules in the total nucleic acid mixture are determined.

Hereinafter, the embodiments of the present invention are described in detail by way of examples. However, it should be understood by those skilled in the art that the following examples are for illustrative purposes and not intended to limit the scope of the invention in any way. Where no specific conditions are given in the examples, conventional conditions or conditions recommended by the manufacturer are followed. The reagents or instruments for which no manufacturers are noted are all common products commercially available.

Example 1: Sequencing of Fetal methylation Marker

First, it should be noted that the fetal methylation marker is one or more differentially methylated genomic regions, the methylation levels of which differ significantly in fetal DNA and maternal DNA, and only slightly among populations.

In this example, 9 samples of placental DNA and paired maternal leukocyte DNA specimens were selected and used for determining the methylation level of a candidate fetal methylation marker, i.e. a region (chr3:50378097-50378226, SEQ ID NO: 1) of the RASSF1A gene, and the individual differences were evaluated. The specific method was as follows.

Bisulfite sequencing PCR (BSP) was used to determine the methylation level of the candidate marker. Specifically, the BSP primer sequences were forward primer GTT-GTTTTTTGGTTGTTTTTTT (SEQ ID NO: 2); and reverse primer CCTACACCCAAATTTCCATTAC (SEQ ID NO: 3). TA cloning and sequencing were then employed to determine the methylation level of the BSP product. Specifically, 30 clones were selected from each specimen for Sanger 3730 sequencing. The methylation level of the candidate marker in the placental DNA and the maternal leukocyte DNA was then calculated, according to m=number of methylated cytosine ($^m$C)/total number of cytosine (C). The experimental results are shown in Table 1 below, in which $m_1$ denotes the methylation level of the candidate marker in the placental DNA; and $m_2$ denotes the methylation level of the candidate marker in the maternal leukocyte DNA.

TABLE 1

| Methylation level of the candidate marker | | |
| --- | --- | --- |
| Sample | $m_1$ | $m_2$ |
| 1 | 82.60% | 0.90% |
| 2 | 87.50% | 0.20% |

TABLE 1-continued

| Methylation level of the candidate marker | | |
|---|---|---|
| Sample | $m_1$ | $m_2$ |
| 3 | 92.80% | 0.40% |
| 4 | 92.90% | 0.20% |
| 5 | 91.60% | 0.00% |
| 6 | 95.20% | 0.40% |
| 7 | 94.40% | 0.80% |
| 8 | 93.50% | 0.20% |
| 9 | 84.80% | 0.20% |
| Average | 90.59% | 0.37% |

Example 2: Quantification of Fetal DNA Concentration

DNA of 6 maternal plasma specimens was extracted using a QIAamp DNA Mini Kit, and the fetal DNA concentration was determined based on the values of $m_1$ and $m_2$ determined in Example 1. The specific steps were as follows.

(1) Bisulfite Treatment

The plasma DNA specimens from the subjects were treated with a bisulfate using the EZ DNA Methylation-Direct™ Kit.

(2) Design of methylation Specific Primers

Two pairs of primers were designed for the marker mentioned in Example 1 and were used in multiplexed QPCR, which included a pair of methylation specific primers and a pair of non-methylation specific primers for specifically amplifying the methylated and non-methylated DNA fragment, respectively. The primer and probe sequences are shown in Table 2 below.

TABLE 2

| Primer and probe sequence | |
|---|---|
| Type of primer or probe | Sequence |
| Methylation specific primer-forward | GATTAGTTGTCGTGTGGGGTTGTAC (SEQ ID NO: 4) |
| Methylation specific primer-reverse | ATCGAAAAAACCTAAACTCATTAAA CTACG (SEQ ID NO: 5) |
| Methylation specific site | TGGTACGTTTTAGTCGGGTGCGGTT (SEQ ID NO: 6) |
| Non-methylation specific primer-forward | GGATTAGTTGTTGTGTGGGGTTGTA T (SEQ ID NO: 7) |
| Non-methylation specific primer-reverse | AAAAAAACCTAAACTCATTAAACTA CAAA (SEQ ID NO: 8) |
| Non-methylation specific site | TGGTGTTTTGTGTGATGTGTAGTGT GTTGG (SEQ ID NO: 9) |

(3) Methylation Specific Multiplexed QPCR

The Sigma JumpStart™ Taq DNA Polymerase was used for multiplexed QPCR, in which the QPCR quantification was carried out using a probe method, the probe used in the methylation specific PCR was marked with FAM and TAMRA, and the probe used in the non-methylation specific PCR was marked with JOE and TAMRA. Specifically, the QPCR system was as follows.

| Reagent | Volume (μL) |
|---|---|
| 10X PCR buffer (containing 15 mM MgCl$_2$) | 2.5 |
| *MgSO$_4$ (50 mM) | 1 |
| dNTP (2.5 mM) | 3 |
| Methylation specific probe (10 μM) | 0.625 |
| Non-methylation specific probe (10 μM) | 0.625 |
| ROX reference dye | 0.5 |
| Mixture of methylation specific primers (both were 10 μM) | 2 |
| Mixture of non-methylation specific primers (both were 10 μM) | 2 |
| JumpStart Polymerase (2.5 U/μL) | 1 |
| Template | 11.75 |
| In total | 25 |

Note:
*indicates that the component may be added or not

The PCR protocol was as follows.

| Temperature | Time | Cycle | Remark |
|---|---|---|---|
| 94° C | 1 min | 1 | Initiation of denaturization |
| 94° C. | 30 s | 45 | Denaturization |
| 60° C. | 30 s | | Anneal |
| 72° C. | 30 s | | Extension |
| 72° C. | 10 min | 1 | Final derivation |
| 4° C. | Forever | 1 | Retention |

(4) Quantification of Fetal DNA Concentration

The ratio of the methylated amplification product to the non-methylated amplification product was calculated by using the $2^{-\Delta\Delta Ct}$ method and then calibrated by a standard curve. The calibrated ratio (represented by R in the formula) was used in the calculation of fetal DNA content in the maternal plasma specimen, where N is defined as the total number of DNA molecules in the parental plasma sample; δ is the fetal DNA content; $m_1$ is the methylation level of the fetal DNA, and $m_1$=90.59%; and $m_2$ is the methylation level of the maternal leukocyte DNA, and $m_2$=0.37%. R and δ are then calculated as follows.

$$R = \frac{\text{Number of methylated of } DNA}{\text{Number of non-methylated } DNA} = \frac{N\varepsilon m_1 + N(1-\varepsilon)m_2}{N\varepsilon(1-m_1) + N(1-\varepsilon)(1-m_2)}, \quad \text{(Formula 1)}$$

and $$\varepsilon = \frac{m_2 + Rm_2 - R}{[R(m_2 - m_1) - (m_1 - m_2)]}.$$

Because $m_2 \approx 0$, ε may be simply calculated as $$\varepsilon = \frac{R}{m_1 + Rm_1}. \quad \text{(Formula 2)}$$

The calculation results are shown in Table 3 below.

TABLE 3

Fetal DNA concentration in maternal plasma specimen

| Sample ID | Estimated fetal concentration (by using Formula 1) | Estimated fetal concentration (by using Formula 2) |
|---|---|---|
| 1 | 0.1554 | 0.1557 |
| 2 | 0.1917 | 0.1918 |
| 3 | 0.1325 | 0.1328 |
| 4 | 0.1230 | 0.1231 |
| 5 | 0.1299 | 0.1300 |
| 6 | 0.0663 | 0.0667 |

Therefore, the fetal DNA concentration in the maternal plasma specimen can be effectively quantified using the method according to the present invention. In addition, the obtained quantification results of the fetal DNA concentration in the parental plasma specimen may be further used to detect abnormalities in the number chromosomes. When the fetal DNA concentration calculated using the methylation difference between the RASSF1A gene on the maternal and fetal chr3 is used to detected an abnormality in the number of chr3, $\varepsilon_{chr3}$ of the test and normal control specimens is calculated, and the test specimen is determined to contain a fetal chr3 trisomy if the $\varepsilon_{chr3}$ of the test specimen is about 1.5. Similarly, the test specimen is determined to contain a fetal chr3 tetrasomy if the $\varepsilon_{chr3}$ of the test specimen is about 2.

Similarly, using the detection of an abnormality in the number of chr21 as an example, a marker (e.g. AIRE, SIM2, ERG and so on) on chr21 is selected and the fetal DNA concentration in the test and normal control samples is quantified using the method above to calculate the $\varepsilon_{chr21}$ of the test and normal control samples. The test specimen is determined to contain a fetal chr21 trisomy if the $\varepsilon_{chr21}$ of the test specimen is about 1.5. Similarly, the test specimen is determined to contain a fetal chr21 tetrasomy if the $\varepsilon_{chr}21$ of the test specimen is about 2. It should be noted that the term "about" as used herein is within ±10%.

Example 3

The cancer cell DNA concentration in a plasma DNA specimen from a patient with colorectal cancer was determined by the method according to the present invention following the steps below. The specific steps were as follows.

(1) Sequencing of predetermined nucleic acid fragment: A colorectal cancer cell DNA and a normal cell DNA specimen were used. For a predetermined nucleic acid fragment from the methylation genes SEPT9, NDRG4, and TFPI2 specific for colorectal cancer, a BSP product was obtained by bisulfite sequencing PCR (BSP), and then the methylation level of the BSP product was determined by TA cloning and sequencing. Specifically, 30 clones were selected from each specimen for Sanger 3730 sequencing. The methylation level of the predetermined nucleic acid fragment in the colorectal cancer cell DNA and normal cell DNA was then calculated, according to m=number of methylated cytosine (${}^mC$)/total number of cytosine (C) or m=number of methylated clones/total number of clones. $m_1$ is the methylation level in the cancer cell DNA and $m_2$ is the methylation level in the normal cell DNA.

(2) Specimen extraction: A plasma DNA sample was extracted from a patient with colorectal cancer using the QIAamp DNA Mini Kit.

(3) Bisulfite treatment: The plasma DNA specimen from the subject was treated with a bisulfite by using the EZ DNA Methylation-Direct™ Kit.

(4) Design of methylation specific primers: For each of the 3 methylation genes SEPT9, NDRG4, and TFPI2 specific for colorectal cancer, two pairs of primers were designed and used in multiplexed QPCR, which included a pair of methylation specific primers and a pair of non-methylation specific primers for specifically amplifying the methylated and non-methylated DNA fragment, respectively. The primer and probe sequences corresponding to the 3 genes are shown in Table 4 below.

TABLE 4

Primer and probe sequences

| Type of primer or probe | ID | Sequence |
|---|---|---|
| Methylation specific primer-forward | SEPT9-M-F | TATTAGTTATTATGTCGGA TTTCGC (SEQ ID NO: 10) |
| Methylation specific primer-reverse | SEPT9-M-R | GCCTAAATTAAAAATCCCG TC (SEQ ID NO: 11) |
| Methylation specific site | M-SEPT9-Probe | TGGAGAGGATTTTGCGGGT GGGTTT (SEQ ID NO: 12) |
| Non-methylation specific primer-forward | SEPT9-U-F | ATTAGTTATTATGTTGGAT TTTGTGG (SEQ ID NO: 13) |
| Non-methylation specific primer-reverse | SEPT9-U-R | AAAACACCTAAATTAAAAA TCCCATC (SEQ ID NO: 14) |
| Non-methylation specific site | U-SEPT9-Probe | TGTGGTTGTGGATGTGTTG GAGAGG (SEQ ID NO: 15) |
| Methylation specific primer-forward | NDRG4-M-F | TTTAGGTTCGGTATCGTTT CGCG (SEQ ID NO: 16) |
| Methylation specific primer-reverse | NDRG4-M-R | CGAACTAAAAACGATACGC CG (SEQ ID NO: 17) |
| Methylation specific site | M-NDRG4-Probe | TCGAGCGTTTATATTCGTT AAATTTACGCGGGTA (SEQ ID NO: 18) |
| Non-methylation specific primer-forward | NDRG4-U-F | GATTAGTTTTAGGTTTGGT ATTGTTTTGT (SEQ ID NO: 19) |
| Non-methylation specific primer-reverse | NDRG4-U-R | AAAACCAAACTAAAAACAA TACACCA (SEQ ID NO: 20) |
| Non-methylation specific site | U-NDRG4-Probe | TTGAGTGTTTATATTTGTT AAATTTATGTGGGTATGTT TTTG (SEQ ID NO: 21) |
| Methylation specific primer-forward | TFPI2-M-F | TCGTTGGGTAAGGCGTTC (SEQ ID NO: 22) |
| Methylation specific primer-reverse | TFPI2-M-R | AAACGAACACCCGAACCG (SEQ ID NO: 23) |

TABLE 4 -continued

Primer and probe sequences

| Type of primer or probe | ID | Sequence |
|---|---|---|
| Methylation specific site | M-TFPI2-Probe | AAAGCGTTTGGCGGGAGGA GGT (SEQ ID NO: 24) |
| Non-methylation specific primer-forward | TFPI2-U-F | TGGTTTGTTGGGTAAGGTG TTT (SEQ ID NO: 25) |
| Non-methylation specific primer-reverse | TFPI2-U-R | ATAAACAAACACCCAAACC ACC (SEQ ID NO: 26) |
| Non-methylation specific site | U-TFPI2-Probe | AAGTGTTTGGTGGGAGGAG GTGTGTGGT (SEQ ID NO: 27) |

(5) Methylation specific multiplexed QPCR: The Sigma JumpStart™ Taq DNA Polymerase was used for multiplexed QPCR, in which the QPCR quantification was carried out using a probe method, the probe used in methylation specific PCR was marked with FAM and TAMRA, and the probe used in non-Methylation specific PCR was marked with JOE and TAMRA.

(6) Quantification of cancer cell DNA concentration: The ratio of the methylated amplification product to the non-methylated amplification product was calculated using the $2^{-\Delta\Delta Ct}$ method and then calibrated by a standard curve. The calibrated ratio (represented by R in the formula) was used to calculate the cancer cell DNA content in the cancer cell specimen, where N is defined as the total number of DNA molecules in the specimen; c is the cancer cell DNA content; $m_1$ is the methylation level of the cancer cell DNA, and approaches 1, and $m_2$ is the methylation level of non-cancer cell DNA in the specimen, and is about 0.

Further $$R = \frac{\text{Number of methylated of } DNA}{\text{Number of non-methylated } DNA} = \frac{N\varepsilon m_1 + N(1-\varepsilon)m_2}{N\varepsilon(1-m_1) + N(1-\varepsilon)(1-m_2)}, \quad \text{(Formula 1)}$$

and $$\varepsilon = \frac{m_2 + Rm_2 - R}{[R(m_2 - m_1) - (m_1 - m_2)]}.$$

can be used to quantify the cancer cell DNA content in the cancer cell specimen. Because $m_2 \approx 0$, $\varepsilon$ may be simply calculated as $$\varepsilon = \frac{R}{m_1 + Rm_1}. \quad \text{(Formula 2)}$$

Consequently, the cancer cell DNA content in the plasma DNA specimen from a patient with colorectal cancer is calculated.

INDUSTRIAL APPLICABILITY

Using the method for determining the nucleic acid composition in a total nucleic acid mixture according to the present invention, the fetal DNA concentration in the maternal and fetal DNA mixture or the cancer cell DNA concentration in the tumor tissue of a tumor patient can be effectively determined with a high degree of accuracy and reliable reproducibility. Moreover, the method can be used to analyze multiple specimens at the same time.

Although specific embodiments of the present invention are described in detail above, it should be understood by those skilled in the art that various modifications and replacements may be made to the details based on the teachings disclosed herein, which all fall within the scope of the present invention defined by the appended claims and equivalents thereof.

In the description of the specification, the description with reference to the terms "an embodiment", "some embodiments", "exemplary embodiments", "example", "specific example", or "some example", and so on, means that specific features, structures, materials or characteristics described in connection with the embodiment or example are included in at least one embodiment or example of the present invention. In the present specification, the illustrative expression of the above terms is not necessarily referring to the same embodiment or example. Moreover, the described specific features, structures, materials or characteristics can be combined in any suitable manner in one or more embodiments.

What is claimed is:

1. A method for determining the nucleic acid composition of a total nucleic acid mixture comprising a first nucleic acid and a second nucleic acid, in which the first nucleic acid and the second nucleic acid are derived from different sources, the method comprising:

1) treating the total nucleic acid mixture with a bisulfite to convert non-methylated cytosine in the total nucleic acid mixture into uracil and to obtain a converted total nucleic acid mixture;

2) subjecting the converted total nucleic acid mixture to multiplexed fluorescent quantitative PCR using a first set of amplification primers and a second set of amplification primers to capture and amplify a predetermined nucleic acid fragment and obtain a ratio R of a methylated amplification product to a non-methylated amplification product of the predetermined nucleic acid fragment wherein the first nucleic acid and the second nucleic acid each contain the predetermined nucleic acid fragment, and the first nucleic acid and the second nucleic acid have different methylation levels in the predetermined nucleic acid fragment; wherein the first set of amplification primers specifically recognizes the predetermined nucleic acid fragment after the non-methylated cytosine in the predetermined nucleic acid fragment is converted into uracil, and the second set of amplification primers specifically recognizes the unconverted predetermined nucleic acid fragment; and wherein a methylation proportion $M_1$=[number of methylated cytosine ($^mC$)/total number of cytosine (C)] of the predetermined nucleic acid fragment in the first nucleic acid and a methylation proportion $M_2$=[number of methylated cytosine ($^mC$)/total number of cytosine (C)] of the predetermined nucleic acid fragment in the second nucleic acid are predetermined using paired control samples that correspond to the first and second nucleic acids; and 3) determining the nucleic acid content ε of the first nucleic acid in the total nucleic acid mixture according to the formula $\varepsilon=(M_2+RM_2-R)/[R(M_2-M_1)-(M_1-M_2)]$ or $\varepsilon=R/[M_1R+M_1]$;

wherein the predetermined nucleic acid fragment is a portion of the RASSF1A gene;

wherein the predetermined nucleic acid fragment further comprises one or more additional predetermined nucleic acid fragments located within one or more genes selected from the group consisting of at least a portion of genes:

SERPINB5, C21orf63, OLIG2, CBR1, SIM2, DSCAM, TRPM2, C21orf29, COL18A1, AIRE, ERG, CD48, FAIM3, ARHGAP25, BMP3, VIM, NDRG4, TFPI2, SFRP2, SEPT9, and SELPLG, and wherein the first set of amplification primers comprise the nucleotide sequences of SEQ ID NOs: 7 and 8.

2. The method according to claim 1, wherein the total nucleic acid mixture contains DNAs from maternal plasma, the first nucleic acid is a fetal DNA, and the second nucleic acid is a maternal DNA.

3. The method according to claim 1, wherein the first nucleic acid is a cancer cell DNA, and the second nucleic acid is a non-cancer cell DNA.

4. The method according to claim 1, wherein $M_1$ is at least 10×, or at least 50× the value of $M_2$.

5. The method according to claim 1, wherein for each gene, the predetermined nucleic acid fragment comprises at least one region selected from the group consisting of the following nucleic acid sequences: chr3:50378097-50378226 of the RASSF1A gene; chr21:45703903-45704111 of the AIRE gene; chr21:38078780-38079213 of the SIM2 gene; chr21:39878777-39879107 of the ERG gene; chr1:160681560-160681732 of the CD48 gene; chr1:207096473-207096654 of the FAIM3 gene; chr2:69001823-69002052 of the ARHGAP25 gene; chr12:109028663-109028901 of the SELPLG gene; chr4:81951942-81952808 of the BMP3 gene; chr10:17270431-17272617 of the VIM gene; chr16:58497034-58498595 of the NDRG4; chr7:93519367-93520184 of the TFPI2 gene; chr4:154709513-154710827 of the SFRP2 gene; and chr17:75368689-75370506 of the SEPT9 gene.

6. A method for determining the nucleic acid composition of a total nucleic acid mixture comprising a first nucleic acid and a second nucleic acid, in which the first nucleic acid and the second nucleic acid are derived from different sources, the method comprising:

1) treating the total nucleic acid mixture with a bisulfite to convert non-methylated cytosine in the total nucleic acid mixture into uracil and to obtain a converted total nucleic acid mixture;

2) subjecting the converted total nucleic acid mixture to multiplexed fluorescent quantitative PCR using a first set of amplification primers and a second set of amplification primers to capture and amplify a predetermined nucleic acid fragment and obtain a ratio R of a methylated amplification product to a non-methylated amplification product of the predetermined nucleic acid fragment wherein the first nucleic acid and the second nucleic acid each contain the predetermined nucleic acid fragment, and the first nucleic acid and the second nucleic acid have different methylation levels in the predetermined nucleic acid fragment; wherein the first set of amplification primers specifically recognizes the predetermined nucleic acid fragment after the non-methylated cytosine in the predetermined nucleic acid fragment is converted into uracil, and the second set of amplification primers specifically recognizes the unconverted predetermined nucleic acid fragment and wherein a methylation proportion $M_1$=[number of methylated cytosine ($^mC$)/total number of cytosine (C)] of the predetermined nucleic acid fragment in the first nucleic acid and a methylation proportion $M_2$=[number of methylated cytosine ($^mC$)/total number of cytosine (C)] of the predetermined nucleic acid fragment in the second nucleic acid are predetermined using paired control samples that correspond to the first and second nucleic acids; and 3) determining the nucleic acid content ε of the first nucleic acid in the total nucleic acid mixture according to the formula $\varepsilon=(M_2+RM_2-R)/[R(M_2-M_1)-(M_1-M_2)]$ or $\varepsilon=R/[M_1R+M_1]$;

wherein the predetermined nucleic acid fragment is a portion of the RASSF1A gene;

wherein the predetermined nucleic acid fragment further comprises one or more additional predetermined nucleic acid fragments located within one or more genes selected from the group consisting of at least a portion of genes:

SERPINB5, C21orf63, OLIG2, CBR1, SIM2, DSCAM, TRPM2, C21orf29, COL18A1, AIRE, ERG, CD48, FAIM3, ARHGAP25, BMP3, VIM, NDRG4, TFPI2, SFRP2, SEPT9, and SELPLG; and wherein the second set of amplification primers comprise the nucleotide sequences of SEQ ID NOs: 4 and 5.

7. The method according to claim 6, wherein the total nucleic acid mixture contains DNAs from maternal plasma, the first nucleic acid is a fetal DNA, and the second nucleic acid is a maternal DNA.

8. The method according to claim 6, wherein the first nucleic acid is a cancer cell DNA, and the second nucleic acid is a non-cancer cell DNA.

9. The method according to claim 6, wherein $M_1$ is at least 10×, or at least 50× the value of $M_2$.

10. The method according to claim 6, wherein for each gene, the predetermined nucleic acid fragment comprises at least one region selected from the group consisting of the following nucleic acid sequences: chr3:50378097-50378226 of the RASSF1A gene; chr21:45703903-45704111 of the AIRE gene; chr21:38078780-38079213 of the SIM2 gene; chr21:39878777-39879107 of the ERG gene; chr1: 160681560-160681732 of the CD48 gene; chr1:207096473-207096654 of the FAIM3 gene; chr2:69001823-69002052 of the ARHGAP25 gene; chr12:109028663-109028901 of the SELPLG gene; chr4:81951942-81952808 of the BMP3 gene; chr10:17270431-17272617 of the VIM gene; chr16: 58497034-58498595 of the NDRG4; chr7:93519367-93520184 of the TFPI2 gene; chr4:154709513-154710827 of the SFRP2 gene; and chr17:75368689-75370506 of the SEPT9 gene.

11. A method for determining the nucleic acid composition of a total nucleic acid mixture comprising a first nucleic acid and a second nucleic acid, in which the first nucleic acid and the second nucleic acid are derived from different sources, the method comprising:
1) treating the total nucleic acid mixture with a bisulfite to convert non-methylated cytosine in the total nucleic acid mixture into uracil and to obtain a converted total nucleic acid mixture;
2) subjecting the converted total nucleic acid mixture to multiplexed fluorescent quantitative PCR using a first set of amplification primers and a second set of amplification primers to capture and amplify a predetermined nucleic acid fragment and obtain a ratio R of a methylated amplification product to a non-methylated amplification product of the predetermined nucleic acid fragment; wherein the first nucleic acid and the second nucleic acid each contain the predetermined nucleic acid fragment, and the first nucleic acid and the second nucleic acid have different methylation levels in the predetermined nucleic acid fragment; wherein the first set of amplification primers specifically recognizes the predetermined nucleic acid fragment after the non-methylated cytosine in the predetermined nucleic acid fragment is converted into uracil, and the second set of amplification primers specifically recognizes the unconverted predetermined nucleic acid fragment and wherein a methylation proportion $M_1$=[number of methylated cytosine ($^mC$)/total number of cytosine (C)] of the predetermined nucleic acid fragment in the first nucleic acid and a methylation proportion $M_2$=[number of methylated cytosine ($^mC$)/total number of cytosine (C)] of the predetermined nucleic acid fragment in the second nucleic acid are predetermined using paired control samples that correspond to the first and second nucleic acids; and
3) determining the nucleic acid content $\varepsilon$ of the first nucleic acid in the total nucleic acid mixture according to the formula $\varepsilon=(M_2+RM_2-R)/[R(M_2-M_1)-(M_1-M_2)]$ or $\varepsilon=R/[M_1R+M_1]$;

wherein the predetermined nucleic acid fragment is a portion of the RASSF1A gene;
wherein the predetermined nucleic acid fragment further comprises one or more additional predetermined nucleic acid fragments located within one or more genes selected from the group consisting of at least a portion of genes:
SERPINB5, C21orf63, OLIG2, CBR1, SIM2, DSCAM, TRPM2, C21orf29, COL18A1, AIRE, ERG, CD48, FAIM3, ARHGAP25, BMP3, VIM, NDRG4, TFPI2, SFRP2, SEPT9, and SELPLG; and
wherein a methylation specific probe and a non-methylation specific probe are further used in the multiplexed fluorescent quantitative PCR, wherein the methylation specific probe has the nucleotide sequence of SEQ ID NO: 6, and the non-methylation specific probe has the nucleotide sequence of SEQ ID NO: 9.

12. The method according to claim 11, wherein the methylation specific probe and the non-methylation specific probe are each labeled with at least one marker selected from the group consisting of FAM, JOE, and TAMRA.

13. The method according to claim 11, wherein the total nucleic acid mixture contains DNAs from maternal plasma, the first nucleic acid is a fetal DNA, and the second nucleic acid is a maternal DNA.

14. The method according to claim 11, wherein the first nucleic acid is a cancer cell DNA, and the second nucleic acid is a non-cancer cell DNA.

15. The method according to claim 11, wherein $M_1$ is at least 10×, or at least 50× the value of $M_2$.

16. The method according to claim 11, wherein for each gene, the predetermined nucleic acid fragment comprises at least one region selected from the group consisting of the following nucleic acid sequences: chr3:50378097-50378226 of the RASSF1A gene; chr21:45703903-45704111 of the AIRE gene; chr21:38078780-38079213 of the SIM2 gene; chr21:39878777-39879107 of the ERG gene; chr1: 160681560-160681732 of the CD48 gene; chr1:207096473-207096654 of the FAIM3 gene; chr2:69001823-69002052 of the ARHGAP25 gene; chr12:109028663-109028901 of the SELPLG gene; chr4:81951942-81952808 of the BMP3 gene; chr10:17270431-17272617 of the VIM gene; chr16: 58497034-58498595 of the NDRG4; chr7:93519367-93520184 of the TFPI2 gene; chr4:154709513-154710827 of the SFRP2 gene; and chr17:75368689-75370506 of the SEPT9 gene.

17. The method according to claim 11, wherein the first set of amplification primers comprise the nucleotide sequences of SEQ ID NOs: 7 and 8 and/or the second set of amplification primers comprise the nucleotide sequences of SEQ ID NOs: 4 and 5.

* * * * *

SEQUENCE LISTING

<160> NUMBER OF SEQ ID NOS: 27

<210> SEQ ID NO 1
<211> LENGTH: 130
<212> TYPE: DNA
<213> ORGANISM: Homo sapiens
<220> FEATURE:

<400> SEQUENCE: 1
accagctgcc gtgtggggtt gcacgcggtg ccccgcgcga tgcgcagcgc gttggcacgc     60
tccagccggg tgcggcccctt cccagcgcgc ccagcgggtg ccagctcccg cagctcaatg    120
agctcaggct                                                            130

<210> SEQ ID NO 2
<211> LENGTH: 22

```
<212> TYPE: DNA
<213> ORGANISM: Artificial
<220> FEATURE:
<223> OTHER INFORMATION: Primer

<400> SEQUENCE: 2
gttgtttttt ggttgttttt tt                                          22

<210> SEQ ID NO 3
<211> LENGTH: 22
<212> TYPE: DNA
<213> ORGANISM: Artificial
<220> FEATURE:
<223> OTHER INFORMATION: Primer

<400> SEQUENCE: 3
cctacaccca aatttccatt ac                                          22

<210> SEQ ID NO 4
<211> LENGTH: 25
<212> TYPE: DNA
<213> ORGANISM: Artificial
<220> FEATURE:
<223> OTHER INFORMATION: Primer

<400> SEQUENCE: 4
gattagttgt cgtgtggggt tgtac                                       25

<210> SEQ ID NO 5
<211> LENGTH: 30
<212> TYPE: DNA
<213> ORGANISM: Artificial
<220> FEATURE:
<223> OTHER INFORMATION: Primer

<400> SEQUENCE: 5
atcgaaaaaa cctaaactca ttaaactacg                                  30

<210> SEQ ID NO 6
<211> LENGTH: 25
<212> TYPE: DNA
<213> ORGANISM: Artificial
<220> FEATURE:
<223> OTHER INFORMATION: Methylation specific site

<400> SEQUENCE: 6
tggtacgttt tagtcgggtg cggtt                                       25

<210> SEQ ID NO 7
<211> LENGTH: 26
<212> TYPE: DNA
<213> ORGANISM: Artificial
<220> FEATURE:
<223> OTHER INFORMATION: Primer

<400> SEQUENCE: 7
ggattagttg ttgtgtgggg ttgtat                                      26

<210> SEQ ID NO 8
<211> LENGTH: 29
<212> TYPE: DNA
<213> ORGANISM: Artificial
<220> FEATURE:
<223> OTHER INFORMATION: Primer

<400> SEQUENCE: 8
```
aaaaaaacct aaactcatta aactacaaa                                    29

<210> SEQ ID NO 9
<211> LENGTH: 30
<212> TYPE: DNA
<213> ORGANISM: Artificial
<220> FEATURE:
<223> OTHER INFORMATION: Non-methylation specific site

<400> SEQUENCE: 9
tggtgttttg tgtgatgtgt agtgtgttgg                                   30

<210> SEQ ID NO 10
<211> LENGTH: 25
<212> TYPE: DNA
<213> ORGANISM: Artificial
<220> FEATURE:
<223> OTHER INFORMATION: Primer

<400> SEQUENCE: 10
tattagttat tatgtcggat ttcgc                                        25

<210> SEQ ID NO 11
<211> LENGTH: 21
<212> TYPE: DNA
<213> ORGANISM: Artificial
<220> FEATURE:
<223> OTHER INFORMATION: Primer

<400> SEQUENCE: 11
gcctaaatta aaaatcccgt c                                            21

<210> SEQ ID NO 12
<211> LENGTH: 25
<212> TYPE: DNA
<213> ORGANISM: Artificial
<220> FEATURE:
<223> OTHER INFORMATION: Methylation specific site

<400> SEQUENCE: 12
tggagaggat tttgcgggtg ggttt                                        25

<210> SEQ ID NO 13
<211> LENGTH: 26
<212> TYPE: DNA
<213> ORGANISM: Artificial
<220> FEATURE:
<223> OTHER INFORMATION: Primer

<400> SEQUENCE: 13
attagttatt atgttggatt ttgtgg                                       26

<210> SEQ ID NO 14
<211> LENGTH: 26
<212> TYPE: DNA
<213> ORGANISM: Artificial
<220> FEATURE:
<223> OTHER INFORMATION: Primer

<400> SEQUENCE: 14
aaaacaccta aattaaaaat cccatc                                       26

<210> SEQ ID NO 15
<211> LENGTH: 25
<212> TYPE: DNA
<213> ORGANISM: Artificial

```
<220> FEATURE:
<223> OTHER INFORMATION: Non-methylation specific site

<400> SEQUENCE: 15
tgtggttgtg gatgtgttgg agagg                                              25

<210> SEQ ID NO 16
<211> LENGTH: 23
<212> TYPE: DNA
<213> ORGANISM: Artificial
<220> FEATURE:
<223> OTHER INFORMATION: Primer

<400> SEQUENCE: 16
tttaggttcg gtatcgtttc gcg                                                23

<210> SEQ ID NO 17
<211> LENGTH: 21
<212> TYPE: DNA
<213> ORGANISM: Artificial
<220> FEATURE:
<223> OTHER INFORMATION: Primer

<400> SEQUENCE: 17
cgaactaaaa acgatacgcc g                                                  21

<210> SEQ ID NO 18
<211> LENGTH: 34
<212> TYPE: DNA
<213> ORGANISM: Artificial
<220> FEATURE:
<223> OTHER INFORMATION: Methylation specific site

<400> SEQUENCE: 18
tcgagcgttt atattcgtta aatttacgcg ggta                                    34

<210> SEQ ID NO 19
<211> LENGTH: 29
<212> TYPE: DNA
<213> ORGANISM: Artificial
<220> FEATURE:
<223> OTHER INFORMATION: Primer

<400> SEQUENCE: 19
gattagtttt aggtttggta ttgttttgt                                          29

<210> SEQ ID NO 20
<211> LENGTH: 26
<212> TYPE: DNA
<213> ORGANISM: Artificial
<220> FEATURE:
<223> OTHER INFORMATION: Primer

<400> SEQUENCE: 20
aaaaccaaac taaaaacaat acacca                                             26

<210> SEQ ID NO 21
<211> LENGTH: 42
<212> TYPE: DNA
<213> ORGANISM: Artificial
<220> FEATURE:
<223> OTHER INFORMATION: Non-methylation specific site

<400> SEQUENCE: 21
ttgagtgttt atatttgtta aatttatgtg ggtatgtttt tg                           42
```

```
<210> SEQ ID NO 22
<211> LENGTH: 18
<212> TYPE: DNA
<213> ORGANISM: Artificial
<220> FEATURE:
<223> OTHER INFORMATION: Primer

<400> SEQUENCE: 22
tcgttgggta aggcgttc                                                 18

<210> SEQ ID NO 23
<211> LENGTH: 18
<212> TYPE: DNA
<213> ORGANISM: Artificial
<220> FEATURE:
<223> OTHER INFORMATION: Primer

<400> SEQUENCE: 23
aaacgaacac ccgaaccg                                                 18

<210> SEQ ID NO 24
<211> LENGTH: 22
<212> TYPE: DNA
<213> ORGANISM: Artificial
<220> FEATURE:
<223> OTHER INFORMATION: Methylation specific site

<400> SEQUENCE: 24
aaagcgtttg gcgggaggag gt                                            22

<210> SEQ ID NO 25
<211> LENGTH: 22
<212> TYPE: DNA
<213> ORGANISM: Artificial
<220> FEATURE:
<223> OTHER INFORMATION: Primer

<400> SEQUENCE: 25
tggtttgttg ggtaaggtgt tt                                            22

<210> SEQ ID NO 26
<211> LENGTH: 22
<212> TYPE: DNA
<213> ORGANISM: Artificial
<220> FEATURE:
<223> OTHER INFORMATION: Primer

<400> SEQUENCE: 26
ataaacaaac acccaaacca cc                                            22

<210> SEQ ID NO 27
<211> LENGTH: 28
<212> TYPE: DNA
<213> ORGANISM: Artificial
<220> FEATURE:
<223> OTHER INFORMATION: Non-methylation specific site

<400> SEQUENCE: 27
aagtgtttgg tgggaggagg tgtgtggt                                      28
```